United States Patent [19]
Christian

[11] Patent Number: 5,178,159
[45] Date of Patent: * Jan. 12, 1993

[54] TORQUEABLE GUIDE WIRE ASSEMBLY WITH ELECTRICAL FUNCTIONS, MALE AND FEMALE CONNECTORS ROTATABLE WITH RESPECT TO ONE ANOTHER

[75] Inventor: Jeffrey J. Christian, San Jose, Calif.

[73] Assignee: Cardiometrics, Inc., Mountain View, Calif.

[*] Notice: The portion of the term of this patent subsequent to Oct. 9, 2007 has been disclaimed.

[21] Appl. No.: 549,227

[22] Filed: Jul. 6, 1990

Related U.S. Application Data

[63] Continuation-in-part of Ser. No. 265,909, Nov. 2, 1988, Pat. No. 4,961,433.

[51] Int. Cl.$^5$ .............................................. A61B 5/00
[52] U.S. Cl. ...................................... 128/772; 128/657
[58] Field of Search ................. 128/657, 772; 604/95, 604/164, 280, 282, 283; 439/13, 18, 29, 461, 462, 668, 669, 816, 825

[56] References Cited

U.S. PATENT DOCUMENTS

| | | | |
|---|---|---|---|
| 2,238,834 | 4/1941 | Travers | 439/669 |
| 3,289,149 | 11/1966 | Pawlowski | 439/669 |
| 3,766,512 | 10/1973 | Falbet | 439/669 |
| 4,961,433 | 10/1990 | Christian | 128/772 |

*Primary Examiner*—Randy C. Shay
*Attorney, Agent, or Firm*—Flehr, Hohbach, Test, Albritton & Herbert

[57] ABSTRACT

A guide wire assembly comprising a guide wire with first and second conductors which extend along the length thereof. The guide wire also comprises a flexible cable having first and second conductors which extend along the length thereof. A connector assembly is provided for interconnecting the flexible cable to said guide wire and interconnecting the conductors carried thereby. The connector assembly includes a male connector with a sleeve and a conductive core which is mounted in the sleeve. An insulator is mounted in the sleeve and insulates the conductive core from the sleeve. A conductive band is carried by the insulator and is spaced from the sleeve. The first and second conductors are disposed within the sleeve. The first connector is connected to the conductive core and the second conductor is connected to the conductive band. The connector assembly includes a female connector that has an inner conductive grip which has a cylindrical recess for receiving the conductive core and an outer conductor grip that has a cylindrical band which engages the portion extending forwardly of the inner conductive grip. An insulator is disposed between the inner and outer conductive grips. An insulating case is mounted on the outer conductive grip. First and second conductors are disposed within the case. The first conductor is connected to the inner conductive grip. The second conductor is connected to the outer conductive grip. The female connector receives the male connector and the first conductive grip receives the conductive core in the cylindrical recess of the first conductive grip. The second conductive grip receives the conductive band of the male connector by the cylindrical band receiving portion of the outer conductive grip engagig the band.

23 Claims, 5 Drawing Sheets

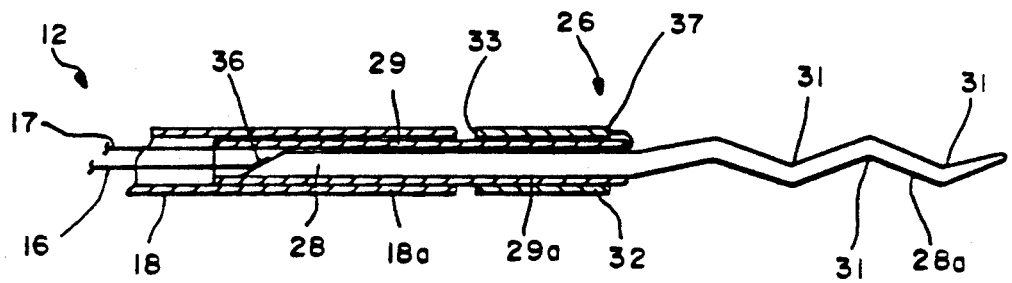
FIG.—1
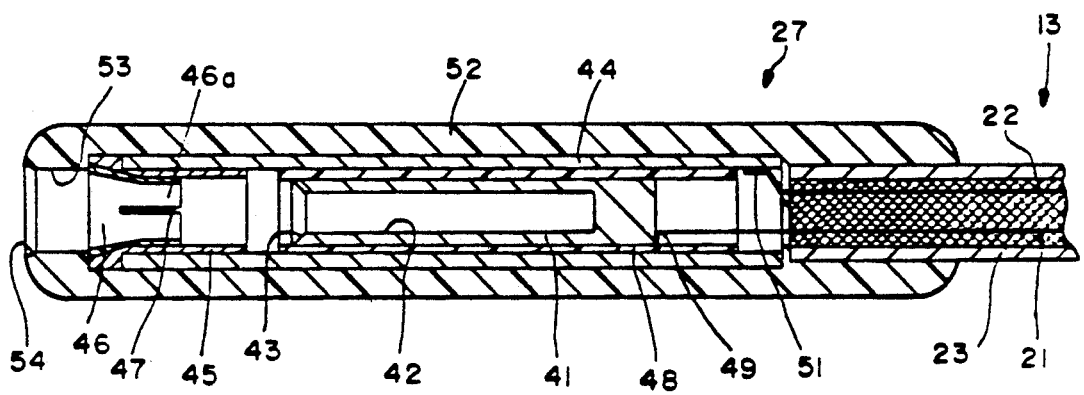
FIG.—2
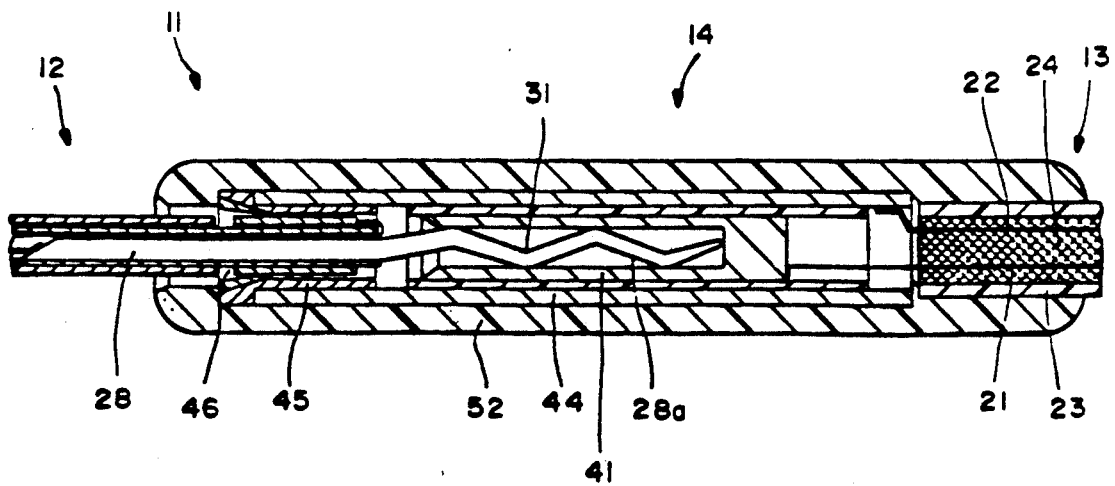
FIG.—3

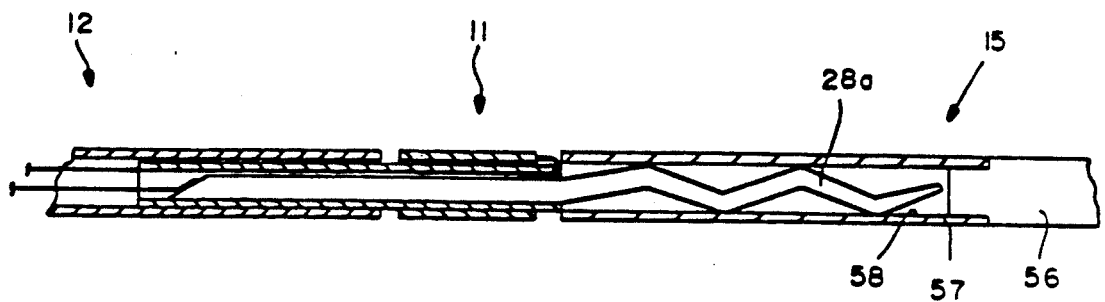
FIG.—4
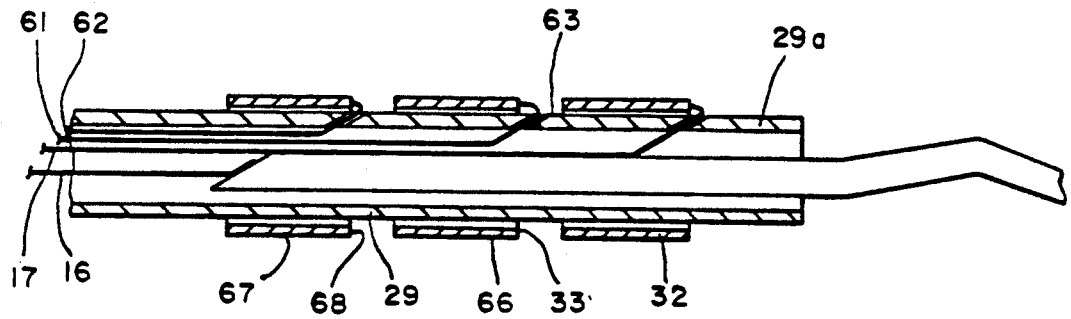
FIG.—5
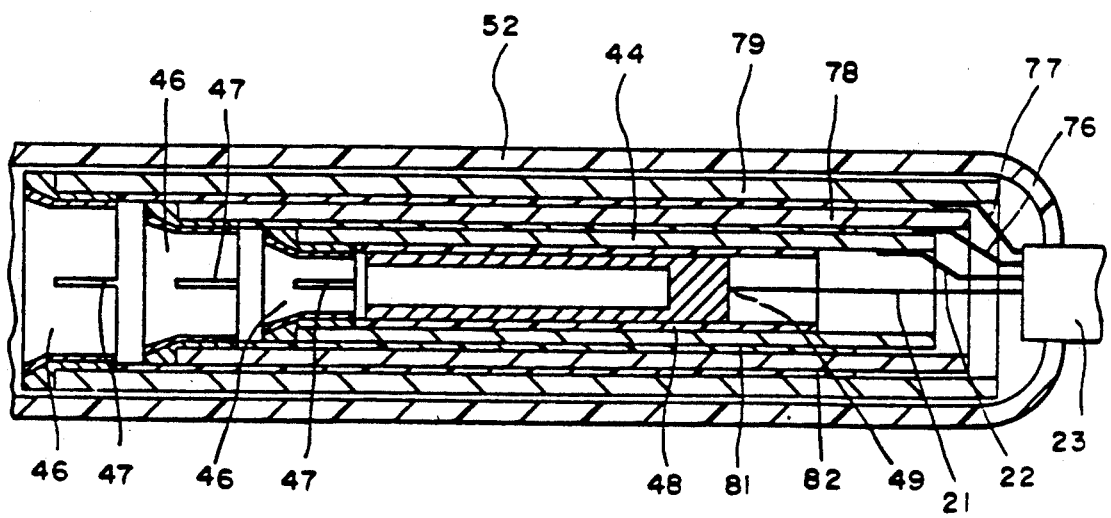
FIG.—6

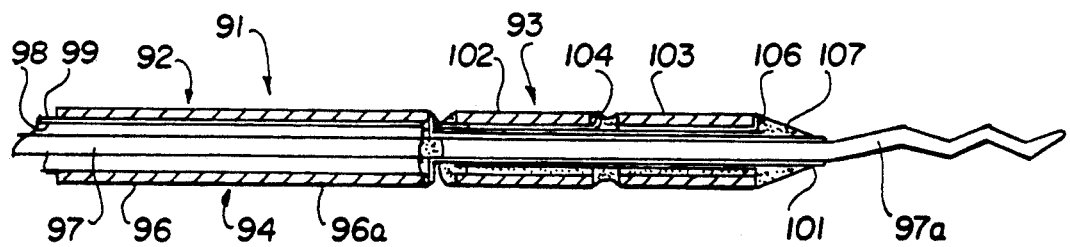
FIG.—7
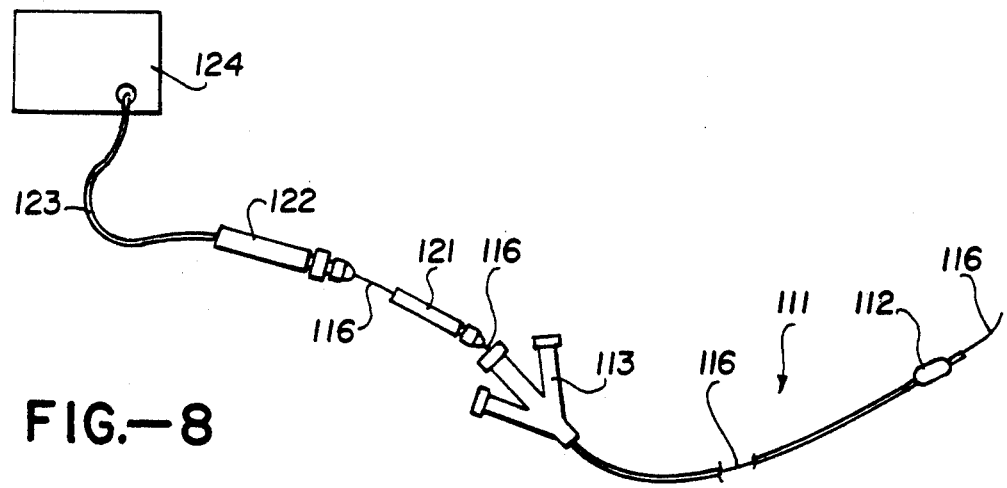
FIG.—8
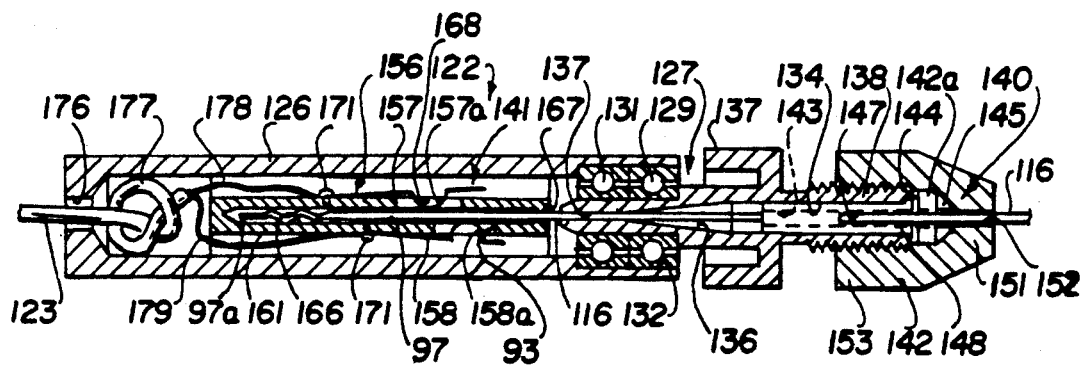
FIG.—9

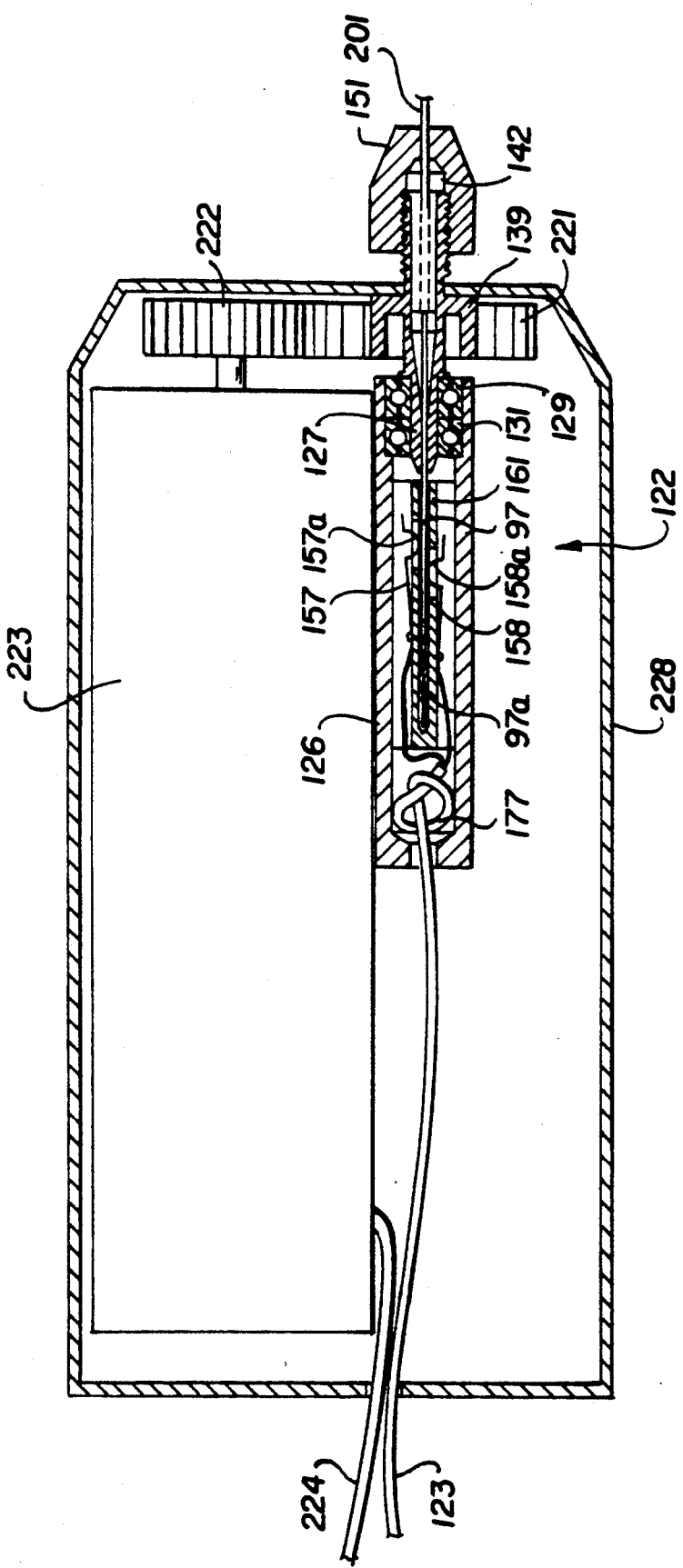
FIG.—13

TORQUEABLE GUIDE WIRE ASSEMBLY WITH ELECTRICAL FUNCTIONS, MALE AND FEMALE CONNECTORS ROTATABLE WITH RESPECT TO ONE ANOTHER

This application is a continuation-in-part of application Ser. No. 265,909, filed on Nov. 2, 1988 now U.S. Pat. No. 4,961,433.

This invention relates to a torqueable guide wire assembly with electrical function and connectors for use therewith and more particularly, such a guide wire assembly with male and female connectors.

Heretofore there has been developed by Advanced Cardiovascular Systems, Inc. and placed on the market a detachable-on-command guide wire system which utilizes a guide wire with a detachable extension guide wire as disclosed in U.S. Pat. No. 4,827,941. This detachable-on-command system utilizes a connector which was comprised of a metallic sleeve into which was fitted a crimped core wire in order to achieve the desired amount of frictional engagement between the guide wire and the extension wire.

A guide wire has been developed as disclosed in co-pending application Ser. No. 411,339 now U.S. Pat. No. 5,105,818 filed on Sept. 22, 1989 which is a continuation-in-part of application Ser. No. 297,111 now U.S. Pat. No. 4,962,753 filed on Jan. 13, 1989 which is a continuation-in-part of application Ser. No. 036,796 abandoned filed Apr. 10, 1987 in which a transducer is carried at the end of a guide wire for making Doppler blood flow measurements which requires the use of first and second conductors extending the length of the guide wire. With such a guide wire a situation may arise where it will be desirable to utilize an extension guide wire to make possible exchange procedures often used in angioplasty. At the present time such exchange procedures are not possible because the connectors and guide wires utilized heretofore do not have conductive functions incorporated therein. There is therefore a need for a guide wire assembly with an electrical function which includes male and female connectors which can be utilized with guide wires and extension wires. Also, in connection with such guide wires it has been found that it is desirable to be able to rotate the guidewire particularly during angioplasty procedures. There is therefore a need for a guidewire which can be torqued.

In general, it is an object of the invention to provide a guide wire assembly with an electrical function and a system and apparatus for utilizing the same.

Another object of the invention is to provide a guide wire assembly of the above character which includes male and female connectors.

Another object of the invention is to provide a guide wire assembly of the above character in which two or more conductors can be provided.

Another object of the invention is to provide a guide wire assembly of the above character which is compatible with the existing guide wire exchange systems.

Another object of the invention is to provide male and female connectors of the above character which are compatible in size with existing guide wires.

Another object of the invention is to provide a guide wire assembly of the above character which can be torqued without interfering with the electrical functions.

Another object of the invention is to provide a guide wire assembly of the above character which utilizes a connector which can be utilized as a torquing device.

Another object of the invention is to provide a guide wire assembly of the above character which utilizes a rotary connector that permits rotation of the guide wire and in which a separate torquing device is utilized on the guide wire.

Another object of the invention is to provide a guide wire assembly and system and apparatus utilizing the same of the above character which permits intravascular ultrasonic imaging.

Additional objects and features of the invention will appear from the following description in which the preferred embodiments are set forth in detail in conjunction with the accompanying drawings.

FIG. 1 is a cross-sectional view of a micro-miniature coaxial connector male for use on a guide wire assembly having an electrical function.

FIG. 2 is a cross-sectional view of a micro-miniature co-axial female connector for use on a guide wire assembly having an electrical function.

FIG. 3 is a cross-sectional view showing the male and female connectors of FIGS. 1 and 2 in mating positions.

FIG. 4 is a cross-sectional view of the male connector of the present invention mated with a female connector of a conventional extension wire.

FIG. 5 is a cross-sectional view of a male connector similar to that in FIG. 1, but with additional conductors.

FIG. 6 is a cross-sectional view of a female connector similar to that in FIG. 2 with additional conductors.

FIG. 7 is a cross-sectional view of a micro-miniature coaxial male connector for use on a guide wire assembly having an electrical function similar to that shown in FIG. 1, but utilizing a continuous core wire.

FIG. 8 is a schematic illustration of a system and apparatus utilizing a torqueable guide wire assembly of the present invention with a rotary connector and a separate torquing device for the guide wire.

FIG. 9 is an enlarged cross sectional view of the rotary connector shown in FIG. 8.

FIG. 13 is a side elevational view in cross section of the proximal extremity of the guide wire assembly shown in FIG. 12 on a reduced scale.

Figure 10:
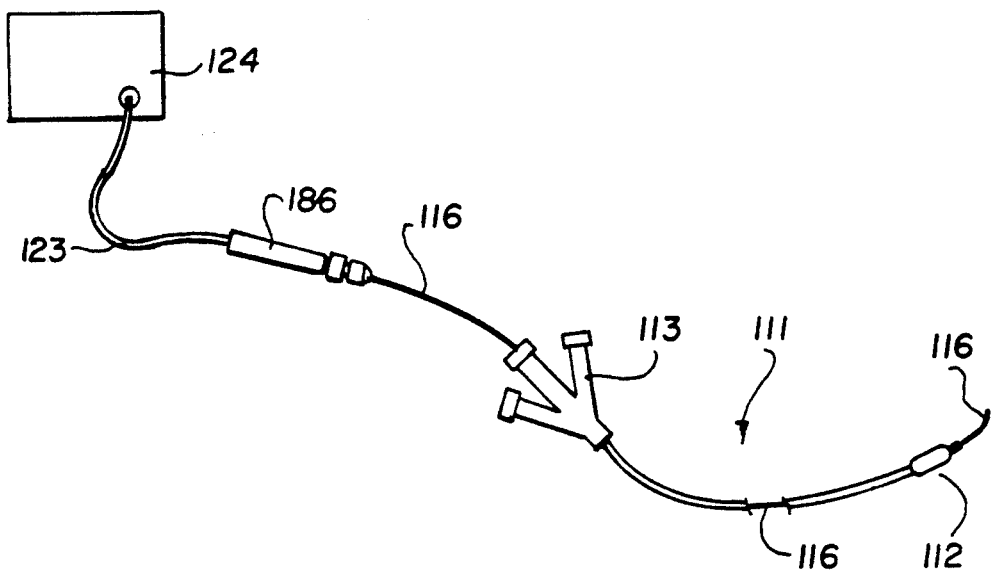
FIG. 10 is another schematic illustration of a system and apparatus utilizing a torquable guide wire assembly of the present invention in which a torquable connector is utilized.

In general, the guide wire assembly of the present invention is comprised of a guide wire in the form of a tubular member having a diameter of 0.018 inches or less and having a proximal extremity. First and second conductors extend along the length of the tubular member. Connector means is connected to the proximal extremity of the tubular member and includes slip ring means for maintaining electrical contact with the first and second conductors during rotation of the guide wire. The guide wire can be torqued by utilizing the connector means as a torquing device or by providing a rotary connector and a separate torquing device attached to the guide wire.

More particularly as shown in the drawings, in FIGS. 1, 2, 3 and 4, the guide wire assembly 11 consists of a guide wire 12 (FIG. 1) and a flexible conducting cable 13 (FIG. 2) which are interconnected by connector means 14 (FIG. 3). Alternatively, the guide wire 12 can be connected to a conventional extension wire 15 (FIG. 4). The guide wire 12, the conducting cable 13 and the connector means 14 are all provided with conductive functions as hereinafter described. The guide wire 12 can be of the type described in U.S. Pat. No. 5,105,818 which is a continuation-in-part of U.S. Pat. No. 4,867,753 which is a continuation-in-part of application Ser. No. 036,796, filed Apr. 10, 1987 now abandoned which can be provided with a transducer (not shown) on its distal extremity which is provided with first and second conductors 16 and 17 which are connected to the transducer and which extend the length of the guide wire internally of the outer sleeve 18. The other details of the construction of the guide wire 12 are disclosed in said references patent and are not disclosed herein because they are not relevant to the present invention. The flexible conducting cable 13 is also provided with first and second conductors 21 and 22 which extend along the length of the flexible conducting cable 13 and are enclosed in a suitable insulating jacket 23 as, for example, one of plastic. Shielding 24 of a suitable type such as formed by braided metal wire may be used if desired to surround the conductors 21 and 22.

The connector means 14 consists of male and female connectors 26 and 2 with the male connector 26 being connected to the guide wire 12 and the female connector being connected to the conducting cable 13. It should be appreciated that the male and female connectors 26 and 27 serve as cooperative mating means and that if desired, the male connector 26 could be connected to the conducting cable 13 and the female connector 27 connected to the guide wire 12.

The male connector 26 is shown in detail in FIG. 1 and consists of a proximal sleeve portion 18a which is a continuation of the sleeve 18 of the guide wire. The sleeve portion 18a has an outside diameter of 0.018 inches or less so that it can be advanced through a conventional angioplasty catheter. It is formed of a suitable material such as stainless steel and has a suitable wall thickness such as 0.002 inches.

A conductive core wire 28 is provided which has its distal extremity disposed within the proximal extremity 18a of the sleeve 18. It has a suitable diameter as, for example 0.010 inches. A sleeve 29 of an insulating material extends over the portion of the core wire 28 disposed within the sleeve portion 18a and serves to insulate the core wire 28 from the sleeve 18a. The sleeve 29 can be formed of a suitable material such as a polyimide. An other suitable thermoplastic material which can be applied can also be utilized for the sleeve. The sleeve 29 is provided with a cylindrical portion 29a which extends proximally of the proximal extremity of the sleeve portion 18a.

The proximal extremity of the core wire 28 is provided with a tapered or probe portion 28a which may be tapered from 0.010 inches down to 0.006 inches. The portion 28a is also crimped as shown to provide a plurality of sharp bends 31 which enhance the frictional fit between the male and female connectors as hereinafter described. The crimped portion is about 1-2 cm long. The conductive core wire 28 can be formed of any suitable conductive material as, for example, stainless steel or beryllium copper which are particularly desirable because of their springiness. A conductive cylindrical member in the form of a band 32 is mounted on the proximal extremity of the insulative sleeve 29 but is spaced therefrom to provide a circumferential air gap 33 which, if desired, can be filled with an adhesive (not shown) which also can serve as an insulator. The band 32 can be formed of a suitable conductive material such as beryllium copper. The first conductor 16 is connected to the distal extremity of the core wire 28 by a solder joint 36. The second conductor 17 extends through the insulating sleeve 29 and over the core wire 28 and is connected to the conductive band 32 at a solder joint 37. Thus it can be seen that the conductive core wire 28 serves as one conductor and the conductive band 32 serves as the other conductor. The male connector 26 hereinbefore described is a micro-miniature coaxial connector that is provided with electrical functions which in particular is capable of providing electrical connections between two separate conductors.

The female connector 27 is shown in detail in FIG. 2 and as shown therein consists of an inner conductive grip 41 formed of a suitable material such as beryllium copper and which is provided with a cylindrical recess 42 which can have a diameter ranging from 0.010 to 0.014 inches and preferably has a diameter of approximately 0.012 inches. The recess 42 is open at its forward extremity which is facing towards the distal extremity of the female connector 27. The recess 42 is provided with a chamfer 43 to facilitate the entry of the crimped conductive core wire portion or probe 28a of the male connector 26 as hereinafter described. An outer conductive grip 44 is provided. It consists of a cylindrical sleeve which is disposed coaxially with respect to the inner conductive grip 41. A shouldered sleeve-like insert 45 is mounted by a press fit in the extremity of the sleeve 44 extending beyond the inner conductive grip. A tapered insert 46 is mounted within the insert 45 and is surrounded with six circumferentially spaced slots 47 which are spaced equally and serve to provide spring-like finger portions 46a which are adapted to engage the conductive band 32 carried by the male connector as hereinafter described. The parts of the outer conductive grip 44 are formed of a suitable conducting material such as beryllium copper. A cylindrical sleeve 48 formed of a suitable insulating material such as a polymeric material is disposed between the inner conductive grip 41 and the outer conductive grip 44 to insulate the same from each other. The sleeve 48 can be formed of a polyimide or other electrically insulating material. The first and second conductors 21 and 22 carried by the conducting cable 13 are connected respectively to the inner conductor grip 41 at a crimped joint 49 and to the second or outer conductive grip by a crimped joint 51. An outer molded case 52 formed of an insulating material such as molded plastic is molded over the outer conductive grip 44 and over the distal extremity of the conducting cable 13. The case 52 is provided with a cylindrical opening 53 which is in axial registration with the outer conductive grip 44 and the inner conductive grip 41. The opening 53 is also provided with a chamfer 54.

From the construction shown in FIG. 2 it can be seen that there has been provided a micro-miniature coaxial female connector 27 which can mate with the male connector 26 as shown in FIG. 1. In mating the male connector 26 with the female connector 27, as shown in FIG. 3 the crimped conductive core wire portion or probe 28a is inserted through the opening 53 in the case 52 into the outer conductive grip 44 and into the cylindrical recess 42 provided in the inner conductive grip 41. The conductive probe 28a frictionally engages the cylindrical side wall of the inner conductive grip forming the recess 42. Continued advancement of the conductive probe 28a into the recess 42 brings the conductive band 32 into engagement with the spring fingers 46a so that they frictionally engage the band and make electrical contact with the outer conductive grip at the same time that a connection is being formed by the probe 28a and the inner conductive grip 41. The frictional engagement is such that the guide wire 12 can be advanced and retracted while still maintaining electrical contact with the conducting cable 13 which is connected to the instrumentation being utilized for making flow, pressure or other measurements.

In using the guide wire assembly 11 in connection with an angioplasty procedure, the coronary guide wire would be positioned within an angioplasty catheter to make blood flow measurements before, during and after the angioplasty procedure. Signals would be supplied from the transducer (not shown) provided on the end of the guide wire assembly through the connector means 14 to the cable 13 to supply the signal to the electrical console (not shown) to provide the flow measurements. Now let it be assumed that it is desirable to change to a large size or even a smaller size dilatation catheter. When this is the case, the female connector 2 is removed from the male connector 26 carried by the guide wire 12. The guide wire 12 is then ready to be attached to a conventional extension guide wire which has approximately the same length as a guide wire, thus doubling the length of the guide wire to make it possible for the guide wire to remain in place while the dilatation catheter previously being used can be removed from the guide wire and a new dilatation catheter of a different size advanced over the guide wire into the coronary system. The distal extremity of a conventional extension guide wire 15 is shown in FIG. 4 in which the guide wire is comprised of a solid stainless steel wire 56 of a suitable outside diameter such as .018 inches which has a sleeve 57 also formed of suitable material such as stainless steel bonded to the distal extremity of the same by suitable means such as welding. The sleeve 57 is provided with a cylindrical recess 58 which is adapted to receive the probe 28a of the male connector 26. Thus, although the male connector 26 is provided with a conducting function it still can function in the same manner as a conventional guide wire to mate with the female connector provided on the distal extremity of the exchange wire 15 so that the exchange wire can be utilized to perform its normal function. It can be seen this has been accomplished without increasing the diameter of the male probe which makes it possible to readily make an exchange of dilatation catheters in a manner well known to those skilled in the field of angioplasty.

As soon as the new size catheter is in place, the extension wire can be removed and the micro-miniature female connector 27 can be reattached to the proximal end of the coronary flow guide wire 12 to establish the electrical connection thereto and to again make it possible to monitor blood flow. Thus it can be seen that the present invention makes it possible to provide monitoring of the blood flow without removing the guide wire carrying the transducer while still making it possible to utilize different size dilatation catheters in the angioplasty procedure.

One of the principal advantages of the guide wire assembly of the present invention and in particular the male and female connectors is that they are of a micro-miniature size and make it possible to provide connectors with more than one conductor and which are still capable of being able to be produced in a size which is 0.018 inches in diameter or less.

In the event that it is necessary to provide more than two conductors in a male micro-miniature connector, the same can be accomplished utilizing the same principles which have been utilized in providing the male and female connectors 26 and 27 shown in FIGS. 1 and 2. Thus as shown in FIG. 5, provision can be readily made for additional conductors, as for example, two conductors 61 and 62 which extend through the sleeve 18 and forwardly through the portion 29a of the insulating sleeve 29 extending through holes 63 provided in the insulating sleeve 29 and soldered to additional bands 66 and 67 formed of the same material as band 32 and spaced apart from the band 32 and being spaced apart from each other by a gap 68. Thus it can be seen that four conductors have been provided with the conductive core wire providing the first conductor and the bands 32, 66 and 67 providing the other three conductors. These additional conductors can be provided without increasing the diameter of the male connector.

The female connector is augmented in a similar way as shown in FIG. 6 to provide additional conductors as, for example, two additional conductors 76 and 77 which are connected to additional outer conductive grips 78 and 79 which are coaxial with the outer conductive grip 44 and which extend forwardly as shown in FIG. 6 so that they are adapted to engage the additional bands and 67 provided on the male connector shown in FIG. 5. An additional insulating sleeve 81 is provided for electrically isolating the second outer conductive grip 78 from the first outer conductive grip 44 and sleeve 82 is provided for electrically isolating the third outer conductive grip 79 from the second outer conductive grip 78. The case 52 surrounds the outer conductive grip 79.

Operation and use of the connectors shown in FIGS. 5 and 6 is substantially identical to that hereinbefore described. The only additional capability being that additional conductors are provided so that additional electrical functions can be performed by the guide wire. From the foregoing it can be seen that a guide wire assembly and connectors for use therein can be provided which can perform electrical functions and which are of a micro-miniature size so that they can be utilized in conjunction with conventional angioplasty catheters and exchange wires. In order to reduce size, a coaxial construction has been utilized for both of the male and female connectors.

Another embodiment of a guide wire assembly 91 incorporating the present invention is shown in FIG. 7 which is comprised of a guide wire 92 having a male connector 93 connected to the proximal extremity 94 of the guide wire. The guide wire 92 is comprised of stainless steel tubing 96 often called hypo tubing having an outside diameter of 0.018 inches or less and having a suitable wall thickness as, for example, 0.002 inches. The hypo tubing can have any suitable length, as for example, approximately 175 centimeters. A core wire 97 which can be of a suitable diameter, as for example, 0.010 inches is disposed in the tubing 96 and extends substantially the entire length thereof of the tubing 96 to provide increased torquing capabilities for the guide wire the core wire typically can be formed of a suitable material such as stainless steel. In connection with the present invention, it need not be conductive, because separate conductive means in the form of first and second conductors 98 and 99 are provided which extend the length of the guide wire 92 and are connected to the transducer or other electrical device at the distal extremity (not shown) of the guide wire assembly 91. As shown in FIG. 7, the conductors 98 and 99 are disposed the concentric space provided between the core wire 97 and the inside wall of the tubing 96.

The core wire 97 extends beyond the proximal extremity 96a of the tubing 96 and has a crimped proximal extremity 97a of the hereinbefore described. An insulating sleeve 101 is provided as formed of a suitable insulating material such as a polyimide hereinbefore described. First and second spaced apart conductive cylindrical members in the form of cylindrical bands 102 and 103 are mounted on the insulating sleeve 101. The conductors 98 and 98 extend between the members 102 and 103 and the conductive core 97 and are secured respectively to the members 102 and 103 by suitable means, such as a solder connections at the proximal extremities thereof as indicated at 104 and 106 in FIG. 7. A suitable adhesive such as that hereinbefore described can be applied at 107 in conical form at the distal extremity of the member 103 to seal the proximal extremity of the male connector 93.

From the foregoing it can be seen that the guide wire assembly 91 differs principally from that shown in FIG. 1 in that the core wire 97 is not utilized as a conductor and that the required electrical conductors are provided by separate conductors provided within the guide wire assembly. As hereinbefore explained, this makes it possible to achieve improving torquing capabilities for the guide wire by having the core wire extend substantially the entire length of the guide wire.

In connection with the male and female connectors hereinbefore provided, it has been found that it is desirable to provide torquing capabilities for the guide wire in certain applications, such as in angioplasty. In angioplasty the physician should be able to rotate the guide wire to enable him to facilitate guiding the guide wire through the tortuous coronary arteries. To make this possible it is necessary to provide a connector which has the capability of providing electrical interconnections while at the same time permitting rotation of the guide wire.

A system and apparatus having such capabilities is shown in FIG. 8 in which a PTCA (percutaneous transluminal coronary angioplasty) catheter 111 is shown commonly used in angioplasty procedures. Such a catheter is provided with an inflatable balloon 112 on its distal extremity and a conventional three-arm fitting 113 on its proximal extremity. A guide wire assembly 116 of the type utilized in the present invention extends through the central arm of the fitting 113 and through the catheter 111 as shown in FIG. 8. A torquing device 121 of a conventional type is mounted on the proximal extremity of the guide wire assembly 116. A rotary connector 122 is removably secured to the proximal extremity of the guide wire assembly 116 proximal of the torquing device and serves to provide electrical connections between the conductors (not shown) in the guide wire assembly 116 and a flexible cable 123 having multiple conductors (not shown) therein connected to a suitable conventional electronic device 124 which operates on the information supplied to and obtained from the conductors in the cable 123 and connected to the conductors in the guide wire assembly. This electronic device 124 can be utilized to perform various functions as, for example, measuring blood velocity, blood flow, blood pressure (static or phasic), ultrasonic imaging and the like.

A detailed cross-sectional view of the rotary connector 122 is shown in FIG. 9. As shown therein, it consists of an elongate cylindrical outer housing 126 formed of a suitable insulating material such as a polymer plastic. A spindle 127 is rotatably mounted in the housing 126 in a suitable manner. For example, it can be Carried by first and second micro-miniature ball bearing assemblies 129 and 131 mounted in a cylindrical recess 132 in the housing 126. A single ball bearing assembly can be utilized for this purpose. However, it has been found that to provide the desired stability for the spindle, it is desirable to utilize two such micro-miniature ball bearing assemblies. If desired, precision bushings may be used as alternative bearing means. As shown in FIG. 9, the spindle 127 is mounted in the inner races of the ball bearing assemblies 129 and 131 and the outer races are seated in the recess 132. The spindle 127 is provided with a cylindrical bore 134 which opens forwardly through the spindle 127. The bore 134 adjoins a conical recess 136 which adjoins a smaller bore 137 that extends outwardly of the spindle 127. The small bore or hole 137 has a suitable size, as for example, 0.022 to 0.024 inches. The spindle 127 is provided with threads 138 at its outer extremity which surrounds the bore 134. A knurled cylindrical portion 139 is formed integral with the spindle 127 and is adapted to be grasped by the fingers of the hand for rotating the spindle 127 as hereinafter described.

Restraining means 140 is provided for restraining movement of the male connector 93 of the guide Wire assembly 116 relative to the female connector 141 carried by the rotary connector 122. The restraining means 140 includes a removable collet 142 formed of suitable material such as brass which is positioned in the bore 134 and is provided with a central bore 143 extending longitudinally thereof. The collet 142 is provided with an enlarged head portion 142a which is provided with chamfers 144 and 145. The chamfer 144 is adapted to seat against a chamfer or seat 146 provided on the spindle 127 and adjoining the bore 134. The collet 141 is provided with circumferentially spaced slots 147 which are spaced apart a suitable angle, as for example, 90° to provide spaced apart fingers 148. The slots 147 can have a width ranging from 0.012 to 0.016 inches. The chamfer 145 of the collet 142 is adapted to be engaged by a nose cap 151 formed of a suitable material such as plastic which is threaded onto the threads 138 on the spindle 127. The nose cap 151 is provided with a centrally disposed opening 152 which is in alignment with the bore 142 provided in the collet 141. The nose cap 151 is provided with longitudinally extending circumferentially spaced apart ribs 153 which are adapted to facilitate rotation of the nose cap 151 by the hand. Alternatively, if desired, knurling can be provided.

The nose cap 151 is adapted to receive the proximal extremity of the guide wire assembly 116 shown in FIG. 7 so that it can be inserted through the collet 141 of the spindle 127 and into the outer housing 126 where it is adapted to engage cooperative slip ring means 156. The cooperative slip ring means 156 is in the form of yieldable finger members 157 and 158 formed of a suitable material, such as beryllium copper or stainless steel. The finger members 157 and 158 are mounted within the outer housing 126 in a suitable manner. For example, they can be mounted on a member 161 formed of an insulating material which can be formed integral with the outer housing 126 or formed as a separate member mounted within the outer housing 126. The member 161 is provided with a centrally disposed bore 166 of a suitable size, as for example, from 0.020 to 0.024 inches which is provided with a chamfer 167 at its outer extremity which is adapted to receive the male connector 93. As can be seen from FIG. 9, the bore 166 does not extend all the way through the member 161 but has a length so that when the proximal extremity 97a of the core wire 97 engages the end of the bore 166, the cylindrical members 102 and 103 are in registration with openings or slots 168 and 169 through which the yieldable finger members 157 and 158 extend. As can be seen, the slots or openings 168 and 169 are offset in longitudinal and circumferential directions. The spring-like finger members 157 and 158 are provided with U-shaped portions 157a and 158a respectively which extend through the slots 168 and 169 and are adapted to engage the conductive cylindrical members or bands 102 and 103. In order to ensure excellent electrical contact, the finger members 157 and 158, including the U-shaped portions may be gold plated. The finger members 157 and 158 can be secured to the insulating member 161 by suitable means such as screws 171.

If more than two conductors are desired in the guide wire assembly, it can be readily seen that such additional conductors can be readily accommodated by providing additional conductive bands or cylindrical members on the proximal extremity of the guide wire and by providing additional spring-like finger members within the housing 126 which are offset from the other spring-like finger members in longitudinal and circumferential directions.

The cable 123 hereinbefore described extends through a hole 176 provided in the outer housing 126 and has a knot 177 tied therein to permit the cable from being withdrawn from the housing 126. Conductors 178 and 179 forming a part of the cable 123 are connected by suitable means such as the screws 171 to the spring-like fingers 157 and 158 as shown in FIG. 9.

Operation and use of the rotary connector 122 in connection with a guide wire assembly 116 of the present invention in connection with the apparatus and system shown in FIG. 8 may now be briefly described as follows. The PTCA catheter 111 shown in FIG. 8 and the guide wire 116 can be inserted into a patient in a conventional manner. The guide wire assembly 116 can be connected to the electronic device 124 through the use of a rotary connector 122. The torquer 121 is first placed on the guide wire assembly 116 in a conventional manner and thereafter the guide wire is connected to the rotary connector 122. This is accomplished by grasping the proximal extremity of the guide wire assembly and opening the nose cap 151 by rotating it counterclockwise on the threaded spindle 127 and then inserting the male connector 93 of the guide wire assembly 116 into the opening 152 in the nose cap and into the bore 142 of the collet and then into the recess 136 and through the bore 137 and thence through the chamfer 167 and into the bore 166 until the proximal extremity 97a of the core wire 97 has seated against the end of the bore 166. The nose cap 151 is then rotated clockwise to clamp the collet 142 onto the guide wire assembly 116 and to hold it firmly in place and to maintain the longitudinal orientation of the guide wire. In tightening or loosening the nose cap 151, the outer housing 126 can be grasped by one hand with two fingers of that hand while grasping the knurled collar 139 provided on the spindle 127 and with the other hand grasping the nose cap 151 to tighten or loosen the same.

With the guide wire assembly 116 so positioned, the slip ring means 156 provided in the rotary connector 122 will be engaged by having the cylindrical members 102 and 103 in engagement with the spring-like finger members 157 and 158 so that the electronic device 124 can be made operational. While the electronic device is operational and while the rotary connector 122 is connected to the guide wire assembly and the physician grasps the torque device or torquer 121 and manipulates the guide wire in a conventional manner to rotate the same to advance the tip of the guide wire and the guide Wire into coronary arterial vessels. The spindle 127 readily rotates with the guide wire because of its mounting in the spindle bearings 129 and 131. This makes it possible for the attending physician to maintain good tactile feel of the guide wire while controlling and manipulating it and still maintaining electrical contact through the cable 123 connected to the rotary connector 122.

Figure 11:
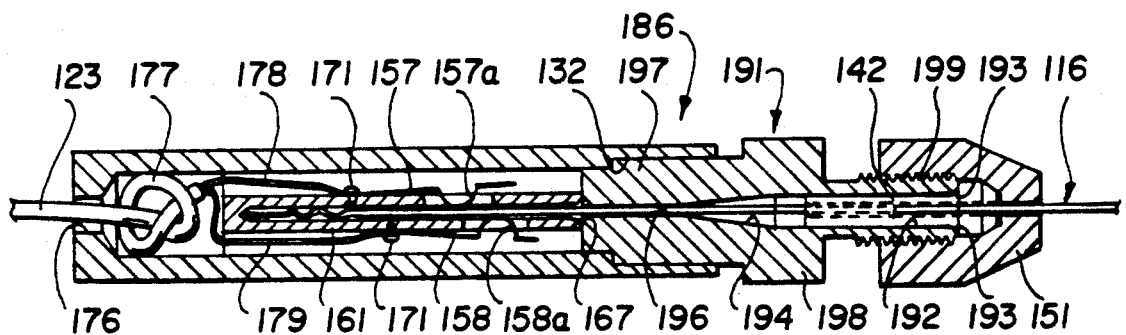
FIG. 11 is a cross sectional view of the torquable connector shown in FIG. 10.

In applications of the present invention where it is not necessary to have complete freedom and rotation of the guide wire 116, a torquer connector 186 can be utilized in the apparatus and system shown in FIG. 10. The use of a separate torquer is eliminated. The torquer connector 186 is shown in FIG. 11 and is very similar to the rotary connector 122 shown in FIG. 9 with the exception that a stationary member 191 has been provided in place of the rotatable spindle 127. The stationary member 191 is provided with a centrally disposed bore 192 which has a chamfer 193 at one end and which opens into a conical passage 194 at the other end. The conical passage 194 opens into a small bore 196 which has a suitable diameter, as for example, 0.020 to 0.024 inches which is in alignment with the bore 166 in the member 161. The stationary member 191 is provided with a boss 197 which is seated in the cylindrical recess 132 in the outer housing 126. The stationary member 191 is also provided with an enlarged knurled portion or member 198. It is also provided with threads 199 which are adapted to be engaged by the nose cap 151 that is adapted to engage the collet 141 provided in the bore 192.

Operation of the torque connector 186 in connection with the system and apparatus shown in FIG. 10 may now be briefly described as follows. The catheter 111 and the guide wire assembly 116 can be inserted in the manner hereinbefore described. An electrical connection can be made to the electrical device 124 by the use of the torquer connector 186 which is connected by taking the proximal extremity of the male connector 93 shown in FIG. 7 into the nose cap 151 and advancing it until it reaches the home position in which the portion 97a of the core wire 97 reaches the terminal extremity of the bore 166 so that the slip ring means 156 formed by the cylindrical members 102 and 103 are in engagement with the spring-like finger members 157 and 158. The nose cap 151 is then tightened by the fingers of one hand while the fingers of the other hand are utilized for holding the knurled member 198 to cause the collet to clamp onto the guide wire 116 in the torquer connector 186. The collet 141 remains stationary with the housing 126 and will not rotate. Since this is the case, the torquer connector 186 can be utilized as a torquer or torquing device. The torquer connector 186 can then be utilized by the attending physician to torque the guide wire. Because any rotation of the guide wire 116 will be applied to the cable 123 extending from the other end of the torquer connector 186, there will be less freedom of movement of the guide wire assembly. For this reason, it is believed that the attending physician would not have as good a tactile feel of what is occurring with the guide wire assembly 116 than with a rotary connector 122 where there is substantially complete freedom of movement because of the use of the bearing mounted spindle 127 and the use of a separate torquer 121. The tactile feel provided, however, should be adequate for many applications.

It should be appreciated that the apparatus and system shown in FIGS. 8 and 10 can be utilized with exchange wires when that becomes necessary. It is merely necessary to remove the proximal extremity of the guide wire 116 from the rotary connector 122 or from the torquer connector 186 and insert the same into the exchange wire. After the exchange operation has been completed, the rotary connector 122 or the torquer connector 186 can be reconnected to the proximal extremity of the guide wire 116.

Figure 12:
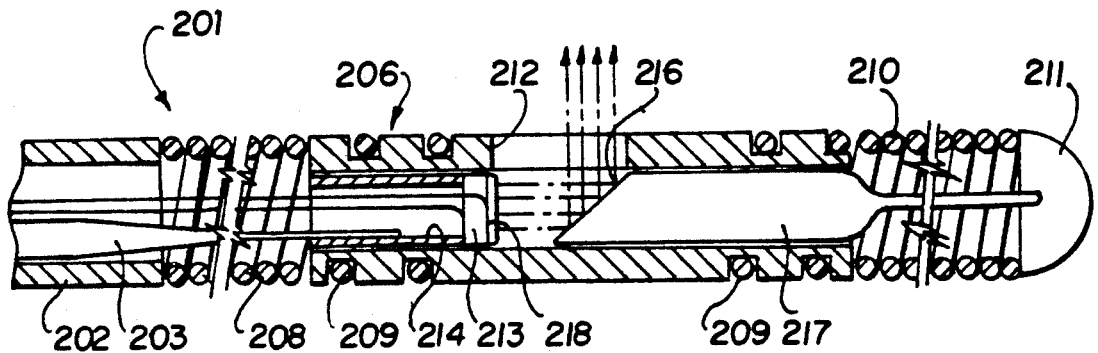
FIG. 12 is an enlarged side elevational view partially in cross section of the distal extremity of a guide wire assembly of the present invention which is provided with intravascular ultrasound imaging capabilities.

It also should be appreciated that the guide wire assembly and the connector assemblies used therewith can be utilized in other applications in which it is desired to transmit and receive electrical signals through the guide wire. An embodiment making possible intravascular ultrasound imaging is shown in FIG. 12 in which a guide wire assembly 201 is provided. The guide wire assembly 201 has an elongate tubular member 202 formed of a suitable material such as stainless steel having an outside diameter of 0.018 inches or less. As hereinbefore described, if desired, a core wire 203 can be provided within the tubular member 202 which extends substantially the entire length of the tubular member to provide additional and torsional rigidity for the tubular member 202. A housing 206 of a suitable material such as stainless steel can be provided separate and apart from the tubular member 201 or alternatively, if desired, it can be formed integral therewith. As shown in FIG. 12, the housing 206 is separate from the distal extremity of the tubular member 201 and is connected thereto by suitable means such as a helical coil spring 208 which is mounted on the distal extremity of the tubular member 202 and to the proximal extremity of the housing 206. The connection to the housing 206 can be by way of a screw-type joint as shown in which the spring 208 is threaded into a helical groove 209 formed on the proximal end of the housing 206. A coil spring tip 210 is secured to the distal extremity of the housing 206 and is provided with a rounded tip 211. The coil spring tip 210 is threaded onto the distal extremity of the housing 206 by threading the same into another helical groove 209. The housing 206 is provided with a cut out 212 in one side wall of the same between the proximal and distal extremities.

Means is provided for directing ultrasonic energy through the cut out 212 and consists of a transducer 213 which is mounted on the proximal side of the cut out 212 and is mounted in the housing 206 by a suitable means such as by attaching the transducer to one end of a stainless steel cylindrical insert 214 by a suitable adhesive. The core wire 203 has its distal extremity bonded to the insert 214 by a suitable adhesive. The conductors 98 and 99 shown in FIG. 7 are connected to the front and back sides of the transducer 213. The ultrasonic energy supplied by the transducer 213 propagates in a direction which is perpendicular to the transducer 213 and strikes an angled mirrored surface 216 which is positioned at a suitable angle, as for example, an angle of 45° to direct the ultrasonic energy out through the cut out 212 in a direction which is generally perpendicular to the longitudinal axis of the housing. The mirrored surface can be provided on a stainless steel insert 217 mounted in the housing 206. The insert 217 can be a short piece of stainless steel wire which has the ground and polished surface 216 thereon. The insert 217 is tapered as shown and has its distal extremity bonded to the rounded tip 211. The mirror surface 216 and the transducer 213 can be positioned apart a suitable distance, as for example, 1 millimeter and can be positioned on the same longitudinal axis. It should be appreciated that with respect to the mirror surface 216, it is possible to grind or lap the surface 216 to provide a surface which can be utilized for focusing the beam, as for example, a concave surface. In order to provide improved resolution, a matching layer 218 is provided on the transducer 213.

In the present invention, it is preferable to have the imaging device be approximately 3 to 5 centimeters proximal from the distal extremity of the tip of the catheter. This makes it possible to place a floppy guide wire tip as shown distal to the housing 206.

In order to achieve imaging through 360° of the vessel in which the guide wire assembly 201 is inserted, the guide wire assembly 201 can be rotated at an appropriate speed by placing a gear 221 on the collar 139 of the spindle 127 (see FIG. 13) and then driving the same by another gear 222. The gear 222 can be driven by a motor 223 of a conventional type controlled through wiring 224 connected to the electronic device 124 to control the speed of rotation of the guide wire assembly 201. In order to synchronize the rotation of the mirror surface 216 with the rotation of the motor 223 a shaft encoder 226 is provided for measuring shaft rotation which also connected by the wiring 224 to the electronic device 124. The rotary connector 122, the gears 221 and 222, the motor 223 and the encoder 226 are mounted in a housing 228.

Since the guide wire assembly 201 can be readily rotated, because of the rotatable spindle 127 utilized, it is possible to achieve imaging with the guide wire assembly 201 so that it can be used therapeutically and diagnostically. For example, the guide Wire assembly 201 can be utilized in an angioplasty procedure to position the catheter while at the same time providing imaging of the vessel in which the procedure is taking place. Thus it is possible to examine the plaque and visualize the same prior to performing an angioplasty. After the angioplasty has been performed the guide wire assembly 201 can be used to ascertain what has occurred with respect to the plaque in that vessel. With such a device it is possible to obtain cross-sectional imaging of the plaque deposit. In addition, it is possible to ascertain whether any damage had been introduced into the arterial wall by the angioplasty procedure and whether there is any danger of any plaque separating from the arterial wall.

It is apparent from the foregoing that there has been provided in the present invention a torquable guide wire assembly which has electrical functions and in which male and female connectors are provided. The torquable guide wire device can be utilized in a system and apparatus for performing various functions. It is possible with the torquable guide wire assembly of the present invention to provide a guide wire which has substantially and the same tactile feel as a guide wire which has no electrical connections thereto. This makes it possible for a skilled physician to operate in the same manner he has operated previously in angioplasty procedures without having to accommodate differences which would occur when the guide wire is connected electrically to an electronic device. The torquable guide wire assembly is capable of being utilized in different types of systems requiring electrical functions, as for example, in connection with intravascular ultrasound imaging by the guide wire assembly itself.

What is claimed is:

1. In a guide wire assembly, a flexible guide wire having proximal and distal extremities and having first and second conductors extending along the length thereof, a flexible cable having first and second conductors extending along the length thereof, and connector means for interconnecting the flexible cable to said guide wire, said connector means including a male connector and a female connector, said male connector comprising an insulating sleeve, first and second cylindrical conductive members mounted on the sleeve and spaced apart longitudinally along the sleeve, means connecting said first and second conductors of one of said guide wire or of said flexible cable to said first and second cylindrical members, said female connector comprising an insulating member, first and second conductive elements carried by the insulating member and adapted to engage the first and second cylindrical members of the male connector when the female connector receives the male connector to establish electrical connections therebetween and means forming electrical connections between the first and second conductive elements of the female connector and the first and second conductors of the other of said flexible cable or said guide were.

2. A guide wire assembly as in claim 1 together with means carried by the female connector for securing the female connector to the other of said flexible cable or said guide wire so that longitudinal movement of the male connector with respect to the female connector is restrained.

3. A guide wire assembly as in claim 2 together with means engaging the guide wire for performing operations with the guide wire and including a collet and means operating on the collet to cause the collet to clamp onto the guide wire.

4. An assembly as in claim 1 together with means carried by the female connector for permitting rotation of the male connector with respect to the female connector.

5. In a guide wire assembly, a flexible guide wire having a diameter of 0.018 inches or less and having first and second conductors extending along the length thereof, a flexible cable having first and second conductors extending along the length thereof, and connector means for interconnecting the flexible cable to said guide wire, said connector means including a male connector and a female connector, said male connector comprising an insulating sleeve, a core wire mounted in the insulating sleeve and extending therefrom, first and second cylindrical conductive members mounted on the sleeve and spaced apart longitudinally along the sleeve, means connecting said first and second conductors of one of said guide wire or of said flexible cable to said first and second cylindrical members, said female connector comprising an insulating member, first and second conductive elements carried by the insulating member and adapted to engage the first and second cylindrical members of the male connector when the female connector receives the male connector to establish electrical connections therebetween, means forming electrical connections between the first and second conductive elements of the female connector and the first and second conductor of the other of said guide wire or cable, and means carried by the female connector for permitting rotation of the male connector with respect to the female connector, said means for permitting rotation of the male connector with respect to the female connector including a spindle, bearing means for rotatably mounting the spindle and means securing the guide wire to the spindle so that as the guide wire is rotated, the spindle is rotated.

6. An assembly as in claim 5 together with means for rotating the spindle.

7. An assembly as in claim 6 together with means carried by the distal extremity of the guide wire for directing ultrasonic energy from the distal extremity of the guide wire at an angle with respect to the longitudinal axis of a guide wire.

8. In a guide wire assembly, a guide wire in the form of a tubular member having a proximal extremity, first and second conductors extending along the length of the tubular member, a male connector connected to the proximal extremity of the tubular member, the male connector including a cylindrical insulating member, first and second conductive cylindrical members mounted in spaced apart longitudinal positions on said insulating sleeve and means electrically connecting the first and second conductors to the first and second cylindrical members.

9. An assembly as in claim 8 together with a core wire and wherein said core wire extends substantially the entire length of the tubular member.

10. A guide wire as in claim 8, together with a female connector having a bore adapted to receive the male connector, first and second spaced apart longitudinally and circumferentially spring finger members adapted to engage the cylindrical members of the male connector, a cable having first and second conductors and means connecting the first and second conductors of the cable to the spring finger members.

11. A guide wire assembly as in claim 10 together with restraining means carried by the female connector for restraining longitudinal movement of the male connector with respect to the female connector.

12. A guide wire assembly as in claim 11 wherein said restraining means includes a collet and means for causing said collet to clampingly engage and disengage said guide wire.

13. In a guide wire assembly, a guide wire in the form of a tubular member having a diameter of 0.018 inches or less and having a proximal extremity, first and second conductors extending along the length of the tubular member, a male connector connected to the proximal extremity of the tubular member, the male connector including a cylindrical insulating member, a core wire disposed within the insulating sleeve and extending beyond the sleeve, first and second conductive cylindrical members mounted in spaced apart longitudinal positions on said insulating sleeve, means electrically connecting the first and second conductors to the first and second cylindrical members, a female connector having a bore adapted to receive the male connector, first and second spaced apart longitudinally and circumferentially spring finger members adapted to engage the cylindrical members of the male connector, a cable having first and second conductors, means connecting the first and second conductors of the cable to the spring finger members, restraining means carried by the female connector for restraining longitudinal movement of the male connector with respect to the female connector said restraining means including a collet and means for causing said collet to clampingly engage and disengage said guide wire and means carried by the female connector, for permitting rotation of the male connector while it is retained within the female connector.

14. A guide wire assembly as in claim 13 wherein said means permitting rotation includes a spindle and bearing means mounting said spindle in said female connector.

15. A guide wire assembly as in claim 14 together with means for rotating said spindle at a predetermined speed.

16. In a guide wire assembly, a flexible guide wire having first and second conductors extending along the length thereof, a flexible cable having first and second conductors extending along the length thereof, connector means for interconnecting the first and second conductors of the flexible cable and the first and second conductors of the guide wire, said connector means including a male connector and a female connector, and means carried by one of the male and female connectors for permitting rotation of the male connector with respect to the female connector.

17. In a guide wire assembly a flexible guide wire having first and second conductors extending along the length thereof, a flexible cable having first and second conductors extending along the length thereof, connector means for interconnecting the first and second conductors of the flexible cable and the first and second conductors of the guide wire, said connector means including a male connector and a female connector, and means carried by one of the male and female connectors for permitting rotation of the male connector with respect to the female connector, said means for permitting rotation of the male connector with respect to the female connector including a spindle, bearing means for rotatably mounting the spindle and means securing the guide wire to the spindle so that as the guide wire is rotated, the spindle is rotated.

18. An assembly as in claim 17 together with means for rotating the spindle.

19. An assembly as in claim 18 together with means carried by the distal extremity of the guide wire for directing ultrasonic energy from the distal extremity of the guide wire at an angle with respect to the longitudinal axis of the guide wire.

20. An assembly as in claim 19 together with restraining means carried by the female connector for restraining longitudinal movement of the male connector with respect to the female connector.

21. An assembly as in claim 20 wherein said restraining means includes a collet and means for causing said collet to clampingly engage and disengage said guide wire.

22. An assembly as in claim 21 together with means carried by the female connector for permitting rotation of the male connector while it is retained within the female connector.

23. A guide wire assembly as in claim 17 together with means for rotating said spindle at a predetermined speed.

* * * * *

UNITED STATES PATENT AND TRADEMARK OFFICE
CERTIFICATE OF CORRECTION

PATENT NO. : 5,178,159

DATED : January 12, 1993

INVENTOR(S) : Jeffrey J. Christian

It is certified that error appears in the above-identified patent and that said Letters Patent is hereby corrected as shown below:

Title page, item [57] Abstract, 2nd col. line 14, [connector] conductor is connected to the conductive core and the In the Abstract, second column, line 19: outer [conductor] conductive grip that has a cylindrical band which Column 3, line 30: connectors 26 and [2] 27 with the male connector 26 being Column 5, line 29: When this is the case, the female connector [2] 27 is re- Column 6, line 34: tional bands 66 and 67 provided on the male connector Column 7, line 1: wire. [t] The core wire typically can be formed of a suitable Column 7, line 10: within the concentric space provided between the core wire 97

UNITED STATES PATENT AND TRADEMARK OFFICE
CERTIFICATE OF CORRECTION

PATENT NO. : 5,178,159
DATED : January 12, 1993
INVENTOR(S) : Jeffrey J. Christian It is certified that error appears in the above-identified patent and that said Letters Patent is hereby corrected as shown below:

Column 7, line 15: ing sleeve 101 is provided [as] and is formed of a suitable insu- Column 7, line 20: ductors 98 and [98] 99 extend between the members 102 and Column 7, line 21: 103 and the [conductive] core wire 87 and are secured respec- Column 7, line 25: adhesive 107 such as that hereinbefore described can be Column 8, line 46: dle 127 and adjoining the bore 134. The collet [141] 142 is Column 8, line 56: 142 provided in the collet [141] 142. The nose cap 151 is

UNITED STATES PATENT AND TRADEMARK OFFICE
CERTIFICATE OF CORRECTION

PATENT NO. : 5,178,159
DATED : January 12, 1993
INVENTOR(S) : Jeffrey J. Christian It is certified that error appears in the above-identified patent and that said Letters Patent is hereby corrected as shown below:

Column 8, line 63: 7 so that it can be inserted through the collet [141] <u>142</u> of the Column 9, line 62: into the bore [142] <u>143</u> of the collet and then into the recess Column 10, line 14: nected to the guide wire assembly<u>,</u> [and] the physician Column 10, lines 17-18: same to advance the tip of the guide wire [and the guide Wire] into coronary arterial vessels. The spindle 127

Column 10, line 47: adapted to engage the collet [141] <u>142</u> provided in the bore Column 10, line 67: The collet [141] <u>142</u> remains stationary with the housing 126

Column 11, line 39: provide additional [and] torsional rigidity for the tubular

Column 11, line 42: from the tubular member [201] <u>202</u> or alternatively, if desired,

UNITED STATES PATENT AND TRADEMARK OFFICE
CERTIFICATE OF CORRECTION

PATENT NO. : 5,178,159
DATED : January 12, 1993
INVENTOR(S) : Jeffrey J. Christian It is certified that error appears in the above-identified patent and that said Letters Patent is hereby corrected as shown below:

Column 11, line 45: of the tubular member [201] <u>202</u> and is connected thereto by Column 12, line 32: ate speed by placing a gear 221 on the [collar] <u>knurled portion</u> 139 of the Column 12, line 41: which <u>is</u> also connected by the wiring 224 to the elec- Column 12, line 43: 221 and 222, the motor 223 and the encoder [226] are Column 13, line 39: guide [were] <u>wire</u>.

Signed and Sealed this

Fifth Day of July, 1994

Attest:

BRUCE LEHMAN

*Attesting Officer*     *Commissioner of Patents and Trademarks*